United States Patent [19]

Gioffre et al.

[11] Patent Number: 4,592,855

[45] Date of Patent: Jun. 3, 1986

[54] EFFERVESCENT COMPOSITIONS

[75] Inventors: Anthony J. Gioffre, 2451 NW. 30th, Ridgefield, Conn.; Ronald J. Ross, Upper Nyack, N.Y.

[73] Assignee: Union Carbide Corporation, Danbury, Conn.

[21] Appl. No.: 672,350

[22] Filed: Nov. 16, 1984

[51] Int. Cl.$^4$ .................. C11D 17/00; C11D 7/02
[52] U.S. Cl. ...................... 252/89.1; 252/90; 252/174.25; 252/305; 252/350; 424/43; 514/846; 424/49
[58] Field of Search .................. 252/188.31, 184, 305, 252/350, 90, 92, 174.25, 89.1; 424/43, 49; 502/34, 38, 39, 407, 410, 415

[56] References Cited

U.S. PATENT DOCUMENTS

| | | | |
|---|---|---|---|
| 1,616,202 | 2/1927 | Shook | 424/43 |
| 2,979,157 | 4/1961 | Clark | 252/184 |
| 3,250,680 | 10/1966 | Menkart et al. | 424/365 X |
| 3,574,824 | 4/1971 | Echeandia et al. | 424/50 |
| 3,639,568 | 2/1972 | Schmitt | 424/43 |
| 4,066,745 | 1/1978 | Tomlinson et al. | 424/49 |
| 4,132,771 | 1/1979 | Schreiber et al. | 424/52 |
| 4,153,680 | 5/1979 | Seibert | 424/49 |
| 4,159,316 | 6/1979 | Jannezewaki et al. | 424/49 |
| 4,187,287 | 2/1980 | Schreiber et al. | 424/49 |
| 4,193,987 | 3/1980 | Harth et al. | 424/49 |
| 4,209,504 | 6/1980 | Harth et al. | 424/49 |
| 4,272,393 | 6/1981 | Gergely | 252/91 |
| 4,349,533 | 9/1982 | Dent et al. | 424/52 |
| 4,537,764 | 8/1985 | Pellico et al. | 424/50 |

FOREIGN PATENT DOCUMENTS

| | | |
|---|---|---|
| 332142 | 11/1930 | United Kingdom . |
| 1382898 | 11/1971 | United Kingdom . |
| 1382898 | 11/1971 | United Kingdom . |
| 1304090 | 1/1973 | United Kingdom . |
| 2082454A | 3/1982 | United Kingdom . |
| 2109682A | 8/1983 | United Kingdom . |

OTHER PUBLICATIONS

"Reports of the Institute for Medical & Dental Engineering", Nos. 3, 22–35 (1969); 4, 115–128 (1970) and 7, 85–95 (1973).

*Primary Examiner*—Prince E. Willis
*Attorney, Agent, or Firm*—G. L. Wamer

[57] ABSTRACT

Effervescent compositions are provided having an effervescent and cleansing action. The effervescent compositions are formed from an essentially anhydrous base medium and an inorganic oxide material containing an adsorbed gas. Upon contact of the composition with water an effervescent action occurs as the gas is desorbed from the inorganic oxide material.

16 Claims, No Drawings

EFFERVESCENT COMPOSITIONS

The invention relates to the field of effervescent compositions and to the process for providing an effervescent action by employing a gas-containing inorganic oxide material in an essentially anhydrous base medium.

The development and formulation of effervescent compositions has traditionally been effected by use of various in situ chemical reactions which form a gas to provide an effervescent action. This type of acid/base reaction system is disclosed in U.S. Pat. Nos. 1,297,494, 1,262,888, 1,516,398, 2,985,562, 3,772,431, 3,888,976, 3,936,385, 3,962,417, 4,127,645, 4,180,467, 4,406,708 and 4,436,720. The cleansing benefits derived from an effervescent action is well documented in the above patents.

A method for providing an effervescent mouthwash is disclosed in U.S. Pat. No. 3,947,567 wherein a liquified gas is distributed under pressure in an aerosol dispensing container. The release of the pressurized mouthwash results in release of the liquified gas.

Although the aforementioned acid/base and liquified gas methods provide an effervescent action such have not been widely employed. The instant invention provides a novel way to provide effervescence to anhydrous compositions when such are contacted with water.

SUMMARY OF THE INVENTION

Effervescent compositions are disclosed that provide an effervescent/mechanical-cleaning action during use. The effervescent compositions comprise an essentially anhydrous base medium and an inorganic oxide material containing up to about 25 percent by weight of an adsorbed gas, e.g., carbon dioxide. The effervescent compositions also provide an astringent sensation when contacted with the skin as a result of the effervescent cleaning action and when carbon dioxide is the adsorbed gas by the in situ generation of carbonic acid.

DETAILED DESCRIPTION OF THE INVENTION

The invention relates to essentially anhydrous compositions which provide an effervescent action and mechanical cleansing action when contacted with water. This effervescent action is both stimulating when in contact with human skin and provides a mechanical mixing action which enhances cleaning and effective distribution of active components present in the effervescent composition. The effervescent compositions are formed from an essentially anhydrous base medium and a gas-containing inorganic oxide material.

The effervescent compositions of the instant invention are unique in their providing an effervescent action without the need of chemical acid/base reactions. The effervescent compositions are formed by use of an inorganic oxide material, e.g., microporous molecular sieves, having sufficient adsorbed gas such that when contained in an essentially anhydrous composition that is contacted with water that a release of the adsorbed gas occurs to provide an effervescent effect. The inorganic oxide material, preferably a microporous inorganic oxide material, employed in the effervescent compositions are usually at least partially dehydrated, i.e., such materials have had at least a portion of their chemically reactive water removed by thermal or chemical treatment. Such materials may be prepared by calcination of the hydrated materials at temperatures about 100° C. in air or other gas. Dehydration of the inorganic oxide material may be carried out at temperatures below 100° C. when subatmospheric pressures are employed. The dehydrated inorganic oxide materials preferably contain less than about 5 percent by weight water, and more preferably less than about 3 percent by weight.

The effervescent compositions of the instant invention comprise an essentially anhydrous base medium and a gas-containing inorganic oxide material. The gas may be any gas capable of being adsorbed by the inorganic oxide material in sufficient effective amount to provide effervescent action upon contacting of the effervescent composition with water. The adsorbed gas is generally present in an amount between about 1 and 25 weight percent of the total weight of the adsorbed gas and inorganic oxide material. Since the effervescent action of the desorbing gas provides a mechanical cleaning and mixing action, it is preferred to have between about 10 and 25 weight percent of the absorbed gas present. Upon contacting the essentially anhydrous effervescent composition with water the adsorbed gas will be released and an effervescent action occurs.

The inorganic oxide material may be any material capable of adsorbing an effective amount of a gas which upon contact with water desorbs the gas in favor of the adsorption of water. The inorganic oxide material can be any of the zeolitic aluminosilicates capable of adsorbing an effective amount of a gas, an aluminophosphate, e.g., as disclosed in U.S. Pat. No. 4,310,440, a silicoaluminophosphate, e.g., as disclosed in U.S. Pat. No. 4,440,871, aluminas, silicas, silica-aluminas and the like. The inorganic oxide material is preferably a microporous material since microporous materials demonstrate gas adsorption characteristics as a result of the pore structure of the material. Representative of such materials are silicalite, zeolite A, zeolite B, zeolite X, zeolite Y, zeolite P, zeolite W, zeolite L, zeolite F, ZSM-type zeolites, natural zeolites such as analcite, chabazite, clinoptilolite, errionite, pawlingite, priolite, ferrierite, mordenite, levynite, etc., and mixtures thereof. A detailed discussion of such aluminosilicates and others is set forth in "ZEOLITE MOLECULAR SIEVES" by Donald W. Breck, Wiley-Interscience Publication (1974). The zeolite may contain cations of alkali metals, alkaline earth metals, zinc, copper, etc., or any other suitable cation. The gas-containing inorganic oxide material may be present in the effervescent composition in an effective amount up to about 99 percent of weight (wt.%) of the total weight of the effervescent composition and such is typically the case when a powdered effervescent composition is desired. The effervescent compositions preferably contain between about 1 wt.% and about 60 wt.% and more preferably between about 5 wt.% and about 50 wt% of the gas-containing inorganic oxide material. The gas-containing inorganic oxide material may also act as an abrasive. The particle size of the gas-containing inorganic oxide material is preferably less than 10 microns and preferably has a particle size distribution with less than 10 percent, more preferably less than 5 percent by weight of the particles having a mean particle diameter greater than 5 microns.

The gas to be employed on this instant invention may be any gas which is a gas at 18° C. and above and which when adsorbed by the inorganic oxide material will then desorb upon being contacted with water. The gas may be, but is not limited to, nitrogen, oxygen, helium, argon, carbon dioxide, fluorine, chlorine and the like and mixtures thereof. The preferred gas for compositions which contact the skin is carbon dioxide owing to its ability to form carbonic acid when it contacts water and thus provide an astringent effect.

The preferred gas-containing inorganic oxide material is a carbon dioxide-containing inorganic oxide material formed by contacting an at least partially dehydrated material with carbon dioxide under effective conditions that result in the adsorption of carbon dioxide by the inorganic oxide material. The inorganic oxide material will adsorb between about 1 and about 25 percent by weight carbon dioxide, based on the weight of said carbon dioxide and inorganic oxide material. The inorganic oxide material preferably adsorbs between about 5 and about 20 percent by weight carbon dioxide. The preferred zeolites are zeolite A, zeolite B, zeolite X, zeolite Y, zeolite P, Chabazite and mordenite.

The effervescent compositions are formed with an essentially anhydrous base medium as heretofore employed in the formulations of anhydrous compositions. The term "essentially anhydrous" is meant to denote a composition, i.e., base-medium that has a water content sufficiently low so as not to cause the adsorbed gas to be desorbed from the inorganic oxide material prior to contact with water. U.S. Pat. No. 3,250,680, incorporated herein by reference thereto, discloses a number of such anhydrous media for hand cleansers, cleansing creams, hand lotions, toothpaste, beauty masks, all-purpose creams, liquifying cleansing creams, ointments and cream shampoo. Powdered effervescent compositions may also be formed. The essentially anhydrous base medium can include flavor components, coloring agents, polishing agents, thickeners, organic surface-active agents and the like.

In addition to the above, the gas-containing inorganic oxide materials may be employed in essentially anhydrous base media of the type generally employed for preparing detergents, powdered cleansers, liquid cleansers, polishing compositions, toilet bowl cleansers, carpet cleaning compositions, stain removing compositions, oven cleaning compositions and the like. For example, essentially anhydrous detergent compositions may be prepared according to the disclosure of U.S. Pat. No. 4,333,771, incorporated herein by reference thereto, by employing an effective amount of a gas-containing inorganic oxide in accordance with the instant invention. The formulation of such compositions are well known in the art.

Suitable flavoring or sweetening agents or mixture thereof, if any, may be employed in formulating a flavor for the effervescent compositions of the present invention. Examples of suitable flavoring constituents include the flavoring oils, e.g. oils of spearmint, peppermint, wintergreen, sassafras, clove, sage, eucalyptus, marjoram, cinnamon, lemon, lime, grapefruit and orange as well as flavoring aldehydes, esters such as methyl salicylate, alcohols, and higher fatty compounds known in the art. Also useful are such chemicals as menthol, carvone and anethole. Of these, the most commonly employed are the oils of peppermint, spearmint, and eucalyptus, and anethole, menthol and carvone. In some cases flavorful solvents, such as chloroform and mock chloroform, may be employed. Such flavorings may be used as liquids or may be solidified by being mixed with a particulate carrier material, such as starch, calcium carbonate, paraffin, vegetable wax, fat, higher fatty acid or other suitable carrier substances. In the cases of solid flavors, such as vanillin, sage, citric acid or licorice, the flavor may be converted to liquid form, if so desired, by dissolving it in the solvent or emulsifying it, usually with the help of a synthetic or natural emulsifying agent. The choice as to whether to utilize particulate solid or liquid flavors or to convert such flavors to a particulate solid or liquid form, respectively, will often depend on the properties desired in the flavor and its compatibility with the sweetener and any other material to be present with it. Suitable sweetening agents include mannitol, sucrose, lactose, maltose, sorbitol, xylitol, sodium cyclamate, saccharin, the dipeptides of the U.S. Pat. No. 3,939,261 and the oxathiazin salts of U.S. Pat. No. 3,932,606. Suitably, flavor and sweetening agent may together comprise from about 0.1 to 10% or more of the compositions of the instant invention.

The effervescent compositions of this invention may also include additional polishing agents of the type commonly employed heretofore as abrasives. Such polishing agents are usually finely divided water insoluble powdered materials. They are generally from 1 to 40 microns, most preferably from 2 to 20 microns in particle sizes, with distribution of normal particle sizes being over the range. Representative polishing agents include, for example, dicalcium phosphate, tricalcium phosphate, insoluble sodium metaphosphate, aluminum hydroxide, colloidal silica, SYLOID 74 (a micron sized synthetic silica) magnesium carbonate, calcium carbonate, calcium prophosphate, bentonite, amorphous alumino-silicate, etc., including suitable mixtures thereof. Such additional polishing agents may be present in an amount up to a maximum of 20% by weight of the formulation and are preferably present in an amount no more than 10%, the amount depending on the desired abrasivity and characteristics of the effervescent composition.

The effervescent compositions of this invention include liquids and solids that maybe proportioned to form a creamy mass of desired consistency which is extrudable from an aerosol or other pressurized container or a collapsible tube (for example aluminum). In general, the liquids in a cream formulation will comprise chiefly glycerine or an oil, propylene glycol, polyethylene glycol 400, etc., including suitable mixtures thereof. The total liquid content will generally be about 20 to 75 percent by weight of the effervescent composition. A gelling agent in cream formulations and gels may be employed, such as the natural and synthetic gums and gum-like materials, for example, Irish moss, gum tragacanth, methyl cellulose, polyvinylpyrrolidone, hydrophilic colloidal carboxyvinyl polymers such as those sold under the trademark Carbopol 934 and 940, hydroxyethyl cellulose, Indian gum, acacia gums, agar agar, locust bean gum, synthetic silicated clays such as those sold under the trademark Laponite CP and Laponite SP, pectin and finely divided pyrogenic silica, sold under the trademarks Cab-O-Sil M5, Syloid 244, Syloid 266 and Aerosol D 200.

The proportions of gelling agents or thickeners in extrudable effervescent compositions are sufficient to form an extrudable, shape-retaining produce which can be squeezed from a tube and substantially maintain its shape thereon. In most cases no more than about 10% of gelling agent need be used and in most instances about 0.5 to 10% will suffice, and preferably about 1 to 5%.

Suitable oils for use in form effervescent compositions include those which have viscosities ranging from about 100 to about 300 centipoises at 70° F. Oils employable herein include mineral oil, light liquid petrolatum thickened to the necessary viscosity; and vegetable oils. A mineral oil commonly employed in cosmetic compositions is Mineral Oil U.S.P. also known as Liquid Petrolatum U.S.P., mineral oil (heavy medicinal) white mineral oil, liquid paraffin, and heavy liquid petrolatum. Mineral oil U.S.P. is defined in Remington's Pharmaceutical Sciences, 13th edition, Mack Publishing Co., Easton, Pa. 1965 as "a mixture of liquid hydrocarbons obtained from petroleum; a colorless transparent, oily liquid, free or nearly free from fluoroescene". It is tasteless and odorless when cold and develops not more than a faint odor or petroleum when heated.

A light liquid petrolatum employable herein is Light Liquid Petrolatum N.F. also known as light liquid paraffin and light white mineral oil It is described in Remington's Pharmaceutical Sciences, as ". . . a mixture of liquid hydrocarbons obtained from petroleum, it may contain a stabilizer". If Light Liquid Petrolatum N.F. is used as the oil it may be thickened to the desired viscosity of from about 100 to about 300 centipoises at 70° F. with one of the well-known commercially available inert thickening materials, such as a pyrogenic silica sold under the trademark Cab-O-Sil, or a hydrogenated castor oil, sold under the tradename THIXIN.

Suitable vegetable oils which may be used as the oil ingredient include coconut oil, cotton-seed oil, sesame oil and similar non-toxic vegetable oils, as described in Vegetable Fats and Oils by E. W. Eckey, Reinhold Publishing Corp., New York, 1954. The vegetable oil is desirably selected to fall within the viscosity range of from about 100 t about 300 centipoises. A particular vegetable oil falling within this range is NEOBFE M-5, a fractional triglyceride of coconut oil. The vegetable oil ingredient may contain a minor amount of an antioxidant such as butylated gydroxyanisole or butylated hydroxytoluene, preferably in an amount ranging from about 0.1% to about 3% by weight, based on the weight of the vegetable oil employed.

The liquid vehicle of an extrudable effervescent composition, together with the gelling agent(s) and other constituents, will form an extrudable mass of a non-dripping consistency when extruded from a collapsible tube, such as an aluminum tube. Thus, by the addition of more vehicle, the effervescent composition can be thinned and conversely, by the addition of more solids, especially more gelling agents and/or the gas-containing material, the effervescent compositions can be thickened. In typical effervescent compositions, the liquid portion comprises glycerine. Although it is preferred to employ glycerine, other suitable vehicles in place thereof or in addition thereto may also be present, either with the mentioned polyhydric alcohols or in replacement for them. Thus, propylene glycol, polyethylene glycol, and polypropylene glycol may be employed providing that they are physiologically acceptable and produce products having a desired refractive index, in the case of the manufacture of visually clear effervescent compositions. The use of glycerine in the liquid vehicle is particularly advantageous in acting with the zeolite component in effecting utilization of the flavor components of the effervescent compositions. Normally the proportion of vehicle is determined by the physical properties of the extrudate. Usually, however, from about 10 to 90% of the vehicle will be employed, with about 10 to 35% being a typical range for the production of opaque formulations and about 40 to 90% being useful for the manufacture of clear formulations.

It is to be understood that while ordinarily where sorbitol or mannitol is employed in compositions, it is used as an aqueous solution, they may be employed herein, with the proviso, however, that it be substantially anhydrous.

The preferred liquid vehicle is an anhydrous humectant or oil selected from the group consisting of glycerine, propylene glycol, polyethylene glycol, polypropylene glycol, liquid light petrolatum, mineral oil, vegetable oil and suitable mixtures thereof.

The gelling agents is desirably selected from the group consisting of sodium carboxymethyl cellulose, hydroxyethyl cellulose, polyvinyl alcohol, Irish moss, silica aerogel or mixtures thereof.

In the preparation of powdered effervescent compositions, it is usually sufficient to admix mechanically, e.g., by milling, the various solid ingredients, in appropriate quantities and particle sizes and thereafter carrying out procedures known in the art for packaging the product.

In chewable effervescent tablets the solids and liquids are proportioned similarly to the amounts above noted and the flavor is blended with the solids and liquids, and a waxy matrix such as polyethylene glycol having a molecular weight of about 6,000 by weight, generally in amounts of about 4–20 percent by weight, in order to facilitate the formation of a table of the desired size and shape.

The listing of polishing agents, and other listings of other components of the effervescent composition given in the present specifications are not intended to be exhaustive and therefore, for other materials of these types reference should be made to a standard handbook, such as Cosmetics: Science and Technology, by Saccharin, 2and printing, 1963, published by Interscience Publishers, Inc.

Organic surface-active agents are generally employed in effervescent compositions to assist in achieving through and complete dispersion of the components of such compositions during use and render the instant compositions more cosmetically acceptable. The organic surface-active material may be anionic, nonionic, ampholytic, or cationic in nature, and it is preferred to employ a surface-active agent which imparts to the composition detersive and foaming properties. Suitably such detergents are water-soluble salts of higher fatty acid monoglyceride monosulfates, such as the sodium salt of the monosulfated monoglyceride of hydrogenated coconut oil fatty acids, higher alkyl sulfates, such as sodium lauryl sulfate, alkyl aryl sulfonates, such as sodium dodecyl benzene sulfonate, higher alkyl sulfoacetates, higher fatty acid ester of 1.2-dihydroxy propane sulfonates, and the substantially saturated high aliphatic acyl amides of lower aliphatic amino carboxylic acid compounds, such as those having 12 to 16 carbon atoms in the fatty acid, or acyl radicals, and the like. Examples of the last mentioned amides are N-lauroyl sarcosine, and the sodium potassium and ethanolamine salts of N-lauroyl, N-myristoyl, or N-palmitoyl sarcosine which should be substantially free from soap or similar higher fatty acid material which tends to substantially reduce the effect of these compounds.

Other suitable surface-active materials include nonionic agents such as condensates of sorbitan monostearate with approximately 20 moles of ethylene oxide, condensates of ethylene oxide with propylene oxide, condensates of propylene glycol ("Pluronics"), and amphoteric agents such a quaternized imidazole derivatives which are available under the trademark "Miranol" such as Miranol C₂M.

Other suitable nonionic detergents are the condensation products of an alpha-olefin oxide containing 10 to 20 carbon atoms, a polyhydric alcohol containing 2 to 10 carbons and 2 to 6 hydroxyl groups and either ethylene oxide or a heteric mixture of ethylene oxide and propylene oxide. The resultant detergents are heteric polymers having a molecular weight in the range of 400 to about 1600 and containing 40% to 80% by weight of ethylene oxide, with an a-olefin oxide to polyhydric alcohol mole ratio in the range of about 1:1 to 1:3. These detergents are manufactured using well-known polymerization techniques under conditions of high temperature and high pressure. These nonionic detergents may be mixed with similar nonionic detergents as well as other types nonionic detergents described herein.

There may also be employed olefin sulfonate detergents, typically long chain alkenyl sulfonates.

It is typical to use an effective amount of at least on surface-active material and generally between about 0.05 and 10% by weight and preferably between about 0.5 and 5% of at least one of the foregoing surface-active materials in the instant oral preparations.

Various other compatible and suitable materials may be incorporated in the effervescent compositions of this invention. Examples thereof are coloring or whitening agents or dyestuffs, preservatives, silicones, chlorophyll compounds, ammonated materials such as urea, diammonium phosphate and mixtures thereof, and other onstituents. In addition, chemical acid/base couples may be employed if additional in situ gas generation is desired, U.S. Pat. No. 3,629,468 is respresentative of such acid/base couples. These adjuvants may be incorporated in the instant effervescent compositions in amounts which do not substantially adversely affect the properties and characteristics desired and are selected and used in proper amount depending upon the particular type of effervescent composition desired.

Antibacterial agents may also be employed in the preparation of the instant effervescent compositions to provide a total content of such agents of up to about 10% by weight, preferably about 0.01 to 5.0% by weight, most preferably about 0.5 to 1.0% by weight, based on the total weight of the effervescent composition.

The effervescent compositions may be prepared by suitably mixing the ingredients. For instance in making a paste composition, a gelling agent such as silica aerogel or Carbopol 934 and a preservative such as dried benzoic acid, if employed, and sweetener, if used, is dispersed with a humectant such as glycerine. An abrasive agent, including the gas-containing inorganic oxide material, surface-active agent and flavor may then separately added and uniformly dispersed. The paste is then thoroughly deareated (e.g., in vacuo) and tubed.

EXAMPLE 1

An carbon-dioxide containing zeolite was prepared using the sodium form of zeolite A. A sample of the zeolite As was placed in a cold air purged oven. The oven was heated to 480° C. and maintained at this temperature for 2 hours to remove water from the zeolite. The oven and sample were then cooled to 300° C. The dehydrated zeolite A was then placed in a container which had been purged with carbon dioxide for fifteen minutes prior to introduction of the dehydrated zeolite. The dehydrated zeolite remained in the container for 2 hours while carbon dioxide was introduced at a pressure of 16 psig. After two hours the container was sealed and the carbon dioxide-containing zeolite maintained under a carbon dioxide atmosphere. A portion of the carbon dioxide-containing zeolite A was analyzed and contained 13.37 percent by weight carbon dioxide, based on the weight of the zeolite.

EXAMPLE 2

Example 1 was repeated except that a Y zeolite was employed instead of zeolite A. A portion of the carbon dioxide-containing zeolite Y was analyzed and contained 15.35 percent by weight carbon dioxide, based on the weight of the zeolite.

EXAMPLE 3

An effervescent composition was prepared using the carbon dioxide-containing Y zeolite prepared in example 2. The effervescent composition was prepared by placing all of the components in a glove box having a nitrogen atmosphere. The preparation was carried out under a nitrogen atmosphere. A slurry was formed by mixing 21.90 grams of the anhydrous carbon dioxide-containing Y zeolite with 26.75 grams of propylene glycol. This slurry was mixed with 0.075 grams benzoic acid, 0.3 grams of a silica sold under the trademark SYLOID 44, 1.00 gram sodium lauryl sulfate, 0.35 grams peppermint oil and 0.75 grams hydroxyl propyl cellulose. The mixture was blended and placed in a desiccator with an aspirator attached thereto. A portion of the final essentially anhydrous composition was added to water and observed to form a foam as carbon dioxide was released from the carbon dioxide-containing Y zeolite.

EXAMPLE 4

Example 3 was repeated except that the carbon dioxide-containing zeolite A of example 1 was employed to form an essentially anhydrous composition. The composition was observed to form a foam upon addition to water as carbon dioxide was released from the carbon dioxide-containing zeolite A.

EXAMPLE 5

Example 4 was repeated except that the peppermint oil was replaced by a sweetner. The toothpaste was observed to foam on being contacted with water as carbon dioxide was released from the carbon dioxide-containing zeolite.

EXAMPLE 6

The effect temperature on the effervescent activity of the effervescent composition of example 4 was evaluated by evaluating the effervescent time for three samples (2 grams each) in 500 milliliters of water at 18° C., 32° C. and 50° C. The three samples were observed and the time recorded at which effervescent began and ended. The results were as follows:

The results indicate that more rapid effervescence occurs at higher temperatures.

We claim:

1. An effervescent composition which upon contacting with water provides effervescent and cleaning action comprising an essentially anhydrous base medium and an effective amount of a gas-containing inorganic oxide material selected from the group consisting of zeolites, aluminophosphates, silicoaluminophosphates and mixtures thereof containing an effective amount of an adsorbed gas between about 1 and about 25 percent by weight to provide effervescence upon contact of the effervescent composition with water.

2. The effervescent composition according to claim 1 wherein said gas-containing inorganic oxide material is selected from the group consisting of zeolite A, zeolite B, zeolite X, zeolite Y, zeolite P, zeolite W, zeolite L, zeolite F, ZSM-type zeolites, silicalite, analcite, chabazite, pauligite, ptilolite, ferrierite, mordenite, levynite, clinoptilolite, errionite, aluminophosphates, silicoaluminophosphates, aluminas, silicas, silica-aluminas and mixtures thereof.

3. The effervescent compositions according to claim 2, wherein the inorganic oxide material is a zeolite containing cations selected from the group consisting of an alkai metal, alkaline earth metal, zinc, copper and mixtures thereof.

4. The effervescent composition according to claim 3, wherein said composition contains a liquid vehicle and said liquid vehicle is polyethylene glycol, mannitol, propylene glycol, sorbitol, liquid light petroleum, mineral oil, vegetable oil, and suitable mixtures thereof.

5. The effervescent composition according to claim 1, which contains an effective amount of a surface-active agent.

6. The effervescent composition according to claim 5 wherein said composition contains between about 0.05 and about 10% by weight of a surface-active agent.

7. The effervescent composition according to claim 5 wherein said surface-active agent is selected from the group consisting of anionic detergents, cationic detergents, nonionic detergents and ampholytic detergents and mixtures thereof.

8. The effervescent composition according to claim 4, which also includes a gelling agent selected from the group consisting of sodium carboxymethyl cellulose, hydroxyethyl cellulose, polyvinyl alcohol, Irish moss, silica aerogel, and mixtures thereof.

9. The effervescent composition according to claim 7, containing 0.5 to 5% of a synthetic anionic surface-active agent.

10. The effervescent composition according to claim 8, which also contains a flavoring agent which is a flavoring oil in an amount of about 0.5 to 2% by weight.

11. The effervescent composition according to claim 1, wherein the composition an essentially anhydrous base medium, an effective amount of a gas-containing inorganic oxide material selected from the group consisting of zeolites, aluminophosphates, silicoaluminophosphates and an abrasive.

12. The effervescent composition according to claim 11, wherein the abrasive is at least one of finely divided silicas, amorphous aluminosilicates and aluminas.

13. The effervescent composition according to claim 1 wherein said effervescent comprises:
(a) between about 5 and about 50 percent by weight of a gas-containing inorganic oxide material selected from the group consisting of zeolite A, zeolite B, zeolite P, zeolite X and mixtures thereof containing between about 1 and about 25 percent by weight of at least one gas selected from the group consisting of nitrogen, oxygen, helium, argon, fluorine, chlorine and carbon dioxide;
(b) at least one liquid vehicle;
(c) at least one surface-active agent; and
(d) at least one gelling agent;

14. The effervescent composition of claim 1 wherein said composition is a powdered composition.

15. An effervescent composition which upon contacting with water provides effervescent and cleaning action comprising an essentially anhydrous base medium and a gascontaining inorganic oxide material containing an effective amount of adsorbed gas to provide effervescence upon contact of the composition with water wherein said inorganic oxide material is selected from the group consisting of the aluminophosphates, silicoaluminophosphates and mixtures thereof.

16. The effervescent composition of claim 15 wherein the gas is selected from the group consisting of nitrogen, oxygen, helium, argon, fluorine, chlorine, carbon dioxide and mixtures thereof.

* * * * *

UNITED STATES PATENT AND TRADEMARK OFFICE
CERTIFICATE OF CORRECTION

PATENT NO. : 4,592,855

DATED : June 3, 1986

INVENTOR(S) : Anthony J. Gioffre and Ronald J. Ross

It is certified that error appears in the above—identified patent and that said Letters Patent is hereby corrected as shown below:

Col. 1, line 10, "in situ" should be -- *in situ* --.

Col. 1, line 39, "in situ" should be -- *in situ* --.

Col. 1, line 68, "about" should be -- above --.

Col. 3, line 17, "Chabazite" should be -- chabazite --.

Col. 4, line 37, "maybe" should be -- may be --.

Col. 4, line 60, "produce" should be -- product --.

Col. 5, line 32, "t" should be -- to --.

Col. 6, line 35, "2and" should be -- 2nd --.

Col. 7, line 31, "onstituents" should be -- constituents --.

Col. 7, line 32, "in situ" should be -- *in situ* --.

Col. 7, line 54, after the word "then" insert -- be --.

Col. 7, line 61, "zeolite As" should be -- zeolite A --.

Col. 8, line 58, after the phrase "The results were as follows:" insert

UNITED STATES PATENT AND TRADEMARK OFFICE
CERTIFICATE OF CORRECTION

PATENT NO. : 4,592,855

DATED : June 3, 1986

INVENTOR(S) : Anthony J. Gioffre and Ronald J. Ross

It is certified that error appears in the above-identified patent and that said Letters Patent is hereby corrected as shown below:

| -- Water Temperature | Initial Effervescence | Ending Effervescence |
|---|---|---|
| 18°C | 35 sec. | 7 min., 53 sec. |
| 32°C | 15 sec. | 7 min., 30 sec. |
| 50°C | 5 sec. | 3 min., 37 sec. |

Col. 10, line 25, "agent;" should be -- agent. --.

Col. 10, line 31, "gascontaining" should be -- gas containing --.

Signed and Sealed this

Twenty-third Day of December, 1986

Attest:

DONALD J. QUIGG

Attesting Officer    Commissioner of Patents and Trademarks